United States Patent [19]  [11] Patent Number: 4,536,478
Sokoloff et al.  [45] Date of Patent: Aug. 20, 1985

[54] METHOD FOR REDUCING NON-SPECIFIC INTERFERENCES IN AGGLUTINATION IMMUNOASSAYS

[75] Inventors: Roger L. Sokoloff, Indianapolis; John M. Reno, Zionsville, both of Ind.

[73] Assignee: Seragan Diagnostics, Inc., Indianapolis, Ind.

[21] Appl. No.: 597,129

[22] Filed: Apr. 5, 1984

[51] Int. Cl.³ .................. G01N 33/54; G01N 33/76
[52] U.S. Cl. .................. 436/533; 436/534; 436/818; 436/825
[58] Field of Search ............ 436/818, 825, 533, 534

[56] References Cited

U.S. PATENT DOCUMENTS

| 3,689,633 | 9/1972 | Sanae | 436/818 X |
| 3,857,931 | 12/1974 | Hager | 436/818 X |
| 4,270,923 | 6/1981 | Kondo | 436/818 X |
| 4,292,038 | 9/1981 | Kondo | 436/825 X |
| 4,362,531 | 12/1982 | de Steenwinkel | 436/825 X |

OTHER PUBLICATIONS

Chemical Abstracts, 95: 165135x, (1981).

Primary Examiner—Sidney Marantz

[57] ABSTRACT

An agglutination immunoassay in which non-specific interferences are reduced by adding to the reaction mixture a halogen substituted carboxylic acid such as chloroacetic acid, dichloroacetic acid, trichloroacetic acid, bromoacetic acid, dibromoacetic acid, tribromoacetic acid, iodoacetic acid and mixtures thereof.

5 Claims, No Drawings

METHOD FOR REDUCING NON-SPECIFIC INTERFERENCES IN AGGLUTINATION IMMUNOASSAYS

BACKGROUND OF THE INVENTION

The present invention is concerned with assay procedures which utilize immunochemical agents such as antigens and antibodies as reactants, as is particularly directed to agglutination immunoassays involving latex carrier particles.

Of the many heterogeneous and homogeneous immunological assay methods now available, agglutination immunoassays continue to be widely used in biology and medicine for the detection of small quantities of an antibody or antigen of interest in a fluid test sample. The agglutination reaction involves the in vitro aggregation of microscopic carrier particles. This aggregation is mediated by the specific reaction between antibodies and antigens, one of which is immobilized on the surface of the carrier particles. In one format, a fluid containing the ligand of interest is introduced into a suspension of the sensitized carrier particles and the appearance of aggregation is noted as indicative of the ligand.

One especially valuable use of the agglutination assays is in the detection of a ligand or analyte of interest in human body fluids such as serum. The agglutination reaction may then be used in several different modes to detect an antigen or antibody (the ligand of interest) as follows:

- with an antigen immobilized carrier particle for the detection of a specific antibody as the ligand of interest;
- with an antibody immobilized carrier particle for the detection of specific antigen or hapten as the ligand of interest;
- in an agglutination inhibition mode using antigen immobilized particles: a fixed quantity of antibody is mixed with a dilution of the test sample containing the ligand of interest. This reaction mixture is then combined with the antigen immobilized carrier particles. The degree to which the ligand of interest (the antigen) in the test sample inhibits the aggregation of the carrier particles that would otherwise have occurred, indicates the concentration of ligand present in the sample;
- in an agglutination inhibition mode with antibody immobilized particles: a fixed quantity of antigen is mixed with a dilution of the test sample containing the ligand of interest—a specific antibody—which inactivates a portion of the antigen. This reaction mixture is then combined with the antibody immobilized carrier particles. The degree to which the ligand (the antibody) present in the test sample inhibits the aggregation of carrier particles, in comparison to that which would otherwise have occurred, indicates the concentration of antibody present.

It has been found, however, that many body fluids such as serum often contain other undefined substances, in addition to the particular ligand or analyte of interest, which cause or inhibit agglutination and thus cause interferences and errors in the assay. Such interferences are nominally called non-specific in that the nature of the interferring agent(s) and the mechanism by which they interfere are poorly understood and no particular causative agent or set of conditions is attributable for these effects. Moreover, interferences of these types cannot be corrected by comparison of the assay results with a similar assay using a sample not containing the ligand or analyte in question as a blank sample because the blank may not be truly representative of the particular serum under test and often the interference is so great that no specific reaction takes place. As a result, much time and effort has been expended in the search for means of eliminating non-specific interferences.

Currently known methods of reducing non-specific interferences in agglutination assays include the following: massive dilution of the test sample up to at least 20-fold; addition of detergents such as are taught in U.S. Pat. No. 4,060,597; rigorous pre-treatment of the test sample including heat treatment for 30 minutes at 56° C. as described by Merz et al, J. Clin. Micro., vol. 5, pg 596, 1977: enzymatic treatment with proteases reaction as described by Collet-Cassart et al, Clin. Chem., vol. 27, 0g 1205, 1981; treatment with reducing/oxidative reagents as described by Cambiaso et al, J. Immuno. Meth., vol. 28, pg 13, 1979 and separation of components using ion exchange chromatography as described in U.S. Pat. No. 4,270,923. While these procedures individually and as a whole are effective, they are time consuming and they can carry with them the undesirable effect of drastically reducing the potential sensitivity and accuracy of the immunoassay as a result of the required manipulations. Another approach has been the addition of specific chemical agents to reduce non-specific interferences in agglutination reactions such as is described within U.S. Pat. No. 4,362,531. The described agents, however, include a wide range of dissimilar and unrelated compounds which are effective to varying degrees in relation to one another. For these reasons, the search for additives to agglutination reaction mixtures which reduce or eliminate the effects of non-specific serum interferences in such immunoassays continues.

SUMMARY OF THE INVENTION

An improved latex immunoassay method is provided to determine the presence of a ligand of interest in a non-extracted body fluid. The improvement comprises the step of: including a chemical additive comprised of at least one halogen substituted carboxylic acid or a salt of the acid in the reaction mixture to decrease non-specific interferences of the latex immunoassay. The additive reduces non-specific interferences in individual serum samples, pooled serum samples and other body fluids for analysis including plasma, saliva, spinal fluid, urine and the like. The addition of such additive permits the use of agglutination immunoassays to determine quantitative levels of endogenous metabolites and to monitor specific ligands of interest such as drugs, therapeutic agents and specific binding proteins in the samples.

DETAILED DESCRIPTION OF THE PREFERRED EMBODIMENT

The present invention is a method of immunoassay which adds a chemical additive to immunochemical reaction mixtures to substantially reduce or eliminate the effects of non-specific serum interferences. The chemical additive comprises at least a halogen substituted carboxylic acid or its salt and is preferably a metallic salt of a trihaloacetic acid such as sodium trichloroacetate. The additives useful in the present invention are defined by Formula I

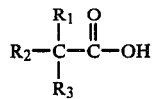

Formula I and wherein $R_1$ is Cl, Br or I and $R_2$ is H, Cl, Br or I and $R_3$ is H, $CH_3-$, $CH_3CH_2-$, Cl, Br or I or a water soluble salt of the acid of Formula I such as the sodium salt. The addition of the compound of Formula I, e.g., sodium trichloroacetate (hereinafter NaTCA) in agglutination reaction mixtures substantially reduces or eliminates completely the effects of non-specific inhibitors and other interferneces in serum and non-serum bodily fluid test samples. The preferred reagents are chloroacetic acid, dichloroacetic acid, trichloroacetic acid, bromoacetic acid, dibromoacetic acid, tribromoacetic acid, iodoacetic acid or mixtures thereof with NaTCA being the most preferred additive. The effects of NaTCA on serum samples in particular are such that increasing the concentration of the additive in concentrations ranging from 0.01 M to 2.0 M with serum concentrations up to about 50% consistently reduced the effect of non-specific interferences. This effect is consistent and reproducible even with serum concentrates which increase the degree of non-specific interference proportionately. Thus, combining comparably large quantities of NaTCA with proportionately larger volumes of serum is practically useful and economical to determine the presence of a ligand of interest in the sample and to eliminated the non-specific inhibitors and interferneces normally encountered during the assay procedure. In normal practice, it has been found that mixtures containing 0.5 M NaTCA and 5.0% serum (v/v) are optimum, but any combination of the additive with serum in the above-indicated ranges is useful and effective.

In this invention, the additive is used in a latex agglutination immunoassay (hereinafter LIA) in which a suspension of latex particles ranging from 0.05–1.0 micrometers in diameter covalently bind or tightly absorb a specific binding partner (an antigen or antibody) for the ligand to be determined in the serum sample. The chemical additive, preferably NaTCA is included in the reaction mixture, the addition of the chemical additive will result in an increased level of specificity in the agglutination at the time of measurement. The increased degree of agglutination may then be determined visually or be measured using conventional procedures such as turbidimetry, nephelometry, conventional light scattering techniques, quasielastic scattering methods or angular anisotropic scattering determination.

Unlike additives known in the prior art, NaTCA used as an additive to agglutination mixtures substantially reduces or eliminates all the effects of non-specific serum interferences. The use of such salts of halogen substituted carboxylic acids as chemical additives in immunoassay methods allows the user to monitor ligands of interest in serum or plasma samples including drugs, antibiotics and other therapeutic agents.

It is noted particularly, however, that a metallic salt of trifluoroacetic acid is not suitable as an additive to reduce non-specific interferences. The chemical additive used in this invention can, in fact, be a mixture of two or more metallic salts of halogen substituted carboxylic acids. For example, a mixture of sodium (or potassium) trichloroacetate and sodium (or potassium) tribromoacetate is effective as an additive. It is preferred that the pH of the additive be maintained between 8.0 and 10.0 for maximum effect. This range may be adjusted to accomodate any optimum immunochemical proportions in the individual test system.

The optimum concentration of the additive depends on numerous factors which include a) latex particle composition, b) nature of the antibody and its sensitivity to the additive, c) nature of the antigen or napten and its sensitivity to the additive and d) temperature—all of which define the system. The optimum concentration of the additive must be determined empirically for each system. Conceivably there are some systems which may be completely incompatible with the additive for reasons having nothing to do with interference by serum.

It has been shown that monosubstituted and/or disubstituted halide salts of short chain carboxylic acid are also effective as additives which decrease non-specific interferences in serum test samples.

The following examples illustrate the present invention and are not intended to limit the same.

EXAMPLE I

Sensitivity of Agglutination to Anti-hCG Antibody when Serum, NaTCA or both are Present Agglutination mixtures (0.4 ml, pH 8.0) which contained 0.02 M sodium barbital, 0.15 M NaCl, 0.1% bovine serum albumin, a 1/92 dilution of latex particles coated with hCG (Pregnosis ® latex available from Roche Diagnostics, Nutley, NJ), and serially diluted anti-human chorionic gonadotropin (anti-hCG) antiserum (Miles-Yeda, #67-073) were prepared. Mixtures which included, in addition, 0.44 M NaTCA or 5.0% normal male serum (hCG free) or both were also prepared.

The agglutination mixtures were maintained at 25° C. and turbidimetric measurements performed in a spectrophotometer. Readings of the absorbance at 600 nm were made immediately after combining all components and again after a 30 minute incubation. The change in absorbance during that interval for each mixture was calculated by subtracting the zero time reading from the 30 minute reading. Additionally, appropriate blanks in which antibody was absent were run in parallel, and any nominal change in absorbance was subtracted, resulting in a ΔA value for each mixture (Table I).

TABLE I

| | ΔA VALUES AND PERCENT RESPONSES [ ] AT VARIOUS ANTIBODY DILUTIONS | | | |
|---|---|---|---|---|
| | NaTCA Absent | | NaTCA Present | |
| Antibody Dilution | Serum Absent | Serum Present | Serum Absent | Serum Present |
| 1/4,000 | — | — | 0.2578 [100.0%] | 0.2601 [100.9%] |
| 1/8,000 | 0.2952 [100.0%] | 0.0204 [6.9%] | 0.1588 [61.6%] | 0.1455 [56.4%] |
| 1/16,000 | 0.1635 [55.4%] | 0.0110 [3.7%] | 0.075.1 [29.1%] | 0.0702 [27.2%] |
| 1/32,000 | 0.0754 [25.5%] | 0.0079 [2.7%] | 0.0345 [13.4%] | 0.0362 [14.1%] |
| 1/64,000 | 0.0311 [10.5%] | 0.0051 [1.7%] | 0.0139 [5.4%] | 0.0174 [6.7%] |
| 1/128,000 | 0.0094 [3.2%] | 0.0047 [1.6%] | 0.0046 [1.8%] | 0.0123 [4.8%] |
| | (.2952 = 100% response) | | (.2578 = 100% response) | |

It is apparent from Table I that in the presence of serum and absence of NaTCA, agglutination occurs neither to a significant extent nor to a degree which can be clearly related to the amount of anti-hCG antiserum present. When NaTCA is included in serum-containing mixtures, however, agglutination does occur, and the degree of agglutination is related to the amount of antibody present.

EXAMPLE II

Sensitivity of Agglutination to hCG in the Presence of Serum, NaTCA or both

Incubation mixtures (350 μpH 8.0) which contained 1/7,000 dilution of anti-hCG antiserum (1/3,500 dilution in mixtures containing NaTCA), 0.02 M sodium barbital, 0.15 M NaCl, 0.1% bovine serum albumin and varying amounts of hCG were prepared. Other mixtures which included, in addition, 0.53 M TCA, 5.7% normal male serum (hCG free) or both were also prepared. After a 15 minute incubation period, 50 μof a dilute hCG-latex (Roche) suspension was added to each mixture. (Final dilution of hCG-latex was 1/100.) The turbidity was measured initially and at the end of a 30 minute interval, and ΔA was calculated as described in Example I. (See Table II). All steps were performed at 25° C.

TABLE II

| | ΔA VALUES AND PERCENT RESPONSES [ ] | | | |
|---|---|---|---|---|
| | NaTCA Absent | | NaTCA Present | |
| (mIU hCG/ reaction mixture) | Serum Absent | Serum Present | Serum Absent | Serum Present |
| 0 | 0.2808 | 0.0117 | 0.2783 | 0.2667 |
| | [100.0%] | [4.2%] | [100.0%] | [95.8%] |
| 3.9 | 0.2567 | 0.0220 | 0.2974 | 0.2453 |
| | [94.6%] | [7.8%] | [92.5%] | [88.1%] |
| 7.9 | 0.2137 | 0.0173 | 0.2403 | 0.2276 |
| | [76.1%] | [6.2%] | [86.3%] | [81.8%] |
| 15.9 | 0.1428 | 0.0110 | 0.2014 | 0.1950 |
| | [50.9%] | [3.9%] | [72.4%] | [70.1%] |
| 31.8 | 0.0736 | 0.0073 | 0.1489 | 0.1402 |
| | [26.2%] | [2.6%] | [53.5%] | [50.3%] |
| 62.5 | 0.0301 | 0.0101 | 0.0907 | 0.0821 |
| | [10.7%] | [3.6%] | [32.6%] | [29.5%] |
| 125 | 0.0124 | 0.0095 | 0.0432 | 0.0450 |
| | [4.4%] | [3.2%] | [15.5%] | [16.2%] |
| 250 | 0.0062 | 0.0084 | 0.0172 | 0.0215 |
| | [2.2%] | [3.0%] | [6.2%] | [7.7%] |
| 500 | 0.0040 | 0.0076 | 0.0074 | 0.0124 |
| | [1.4%] | [2.7%] | [2.7%] | [4.5%] |
| 1000 | 0.0000 | 0.0075 | 0.0075 | 0.0064 |
| | [0.0%] | [2.7%] | [2.7%] | [2.3%] |
| | (0.282 = 100% response) | | (0.2783 = 100% response) | |

It is apparent from Table II that in the presence of serum and absence of NaTCA, agglutination occurs neither to a significant extent nor to a degree which can be clearly related to the amount of hCG present. When NaTCA is included in serum-containing mixtures, however, agglutination does occur, and the degree of agglutination is related to the amount of hCG present.

We claim:

1. In an agglutination immunoassay for an analyte in a fluid sample which is combined with a reagent which includes sensitized latex particles and binding partner as required, whereby the degree of agglutination of the particles is a measure of the analyte in the sample, the improvement comprising the step of adding to the reaction mixture an additive to decrease non-specific interferences of the agglutination of the particles, where such additives comprise at least one halogen substituted carboxylic acid or water soluble salt thereof wherein the acid has the formula:

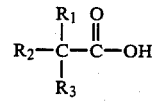

and wherein $R_1$ is Cl, Br or I and $R_2$ is H, Cl, Br or I and $R_3$ is H, $CH_3-$, $CH_3CH_2-$, Cl, Br or I.

2. The method of claim 1 wherein the additive is selected from the group consisting of chloroacetic acid, dichloroacetic acid, trichloroacetic acid, bromoacetic acid, dibromoacetic acid, tribromoacetic acid, iodoacetic acid, a water soluble salt thereof and mixtures thereof.

3. The method of any one of claims 1 or 2 wherein the additive is present in a concentration ranging from 0.01 to 2.0 molar.

4. The method of any one of claims 1 or 2 wherein the additive is present as its water soluble salt.

5. The method of any one of claims 1 or 2 wherein the additive composition is a mixture of at least two of said additives.

* * * * *